United States Patent [19]

Hartung

[11] 4,163,067

[45] Jul. 31, 1979

[54] GLYCYRRHIZIN-FREE FRACTIONS FROM LICORICE ROOT AND PROCESS FOR OBTAINING SUCH FRACTIONS

[75] Inventor: Harold A. Hartung, West Collingswood, N.J.

[73] Assignee: MacAndrews and Forbes Company, Camden, N.J.

[21] Appl. No.: 764,896

[22] Filed: Feb. 2, 1977

Related U.S. Application Data

[63] Continuation-in-part of Ser. No. 695,537, Jun. 14, 1976, abandoned.

[51] Int. Cl.$^2$ .............................................. A23L 1/22
[52] U.S. Cl. .................................. 426/573; 426/592; 426/590; 426/594; 426/578; 426/579; 426/641; 426/589; 426/593; 426/650; 426/655; 426/431; 131/17 R; 260/236.5
[58] Field of Search .................... 260/236.5; 426/650, 426/655, 431, 573, 592, 590, 594, 579, 578, 641, 589, 593

[56] References Cited

U.S. PATENT DOCUMENTS

| | | | |
|---|---|---|---|
| 1,389,663 | 9/1921 | Ito ........................................ | 426/655 |
| 1,849,569 | 3/1932 | Condorelli et al. .................. | 426/655 |
| 2,058,019 | 10/1936 | Ito et al. ........................... | 426/655 X |

FOREIGN PATENT DOCUMENTS 988 of 1859 United Kingdom ..................... 426/655

OTHER PUBLICATIONS

Fenaroli's Handbook of Flavor Ingredients, Edited by Furia et al., 1971, The Chemical Rubber Co., Cleveland, pp. 152, 153.
Food Engineering, vol. 38, No. 5, May 1966, p. 46.

*Primary Examiner*—Joseph M. Golian
*Attorney, Agent, or Firm*—Howson and Howson

[57] ABSTRACT

Glycyrrhizin-free fractions from licorice root are obtained by selective extraction and fractionation. The glycyrrhizin-free fractions are described, as in the manner for obtaining them and uses of the fractions as natural flavorants, flavor potentiators and adjuvants, as surface active agents, including wetting, foaming, emulsifying, dispersing and settling agents. Products containing the glycyrrhizin-free fractions are also described.

13 Claims, No Drawings

GLYCYRRHIZIN-FREE FRACTIONS FROM LICORICE ROOT AND PROCESS FOR OBTAINING SUCH FRACTIONS

BACKGROUND OF THE INVENTION

This application is a continuation-in-part of copending application Ser. No. 695,537 filed June 14, 1976, now abandoned.

Licorice root is the only botanical known to contain appreciable levels of glycyrrhizin which is present in the root as the calcium and potassium salts of glycyrrhizic acid, a glycoside of glycyrrhetic acid. Glycyrrhizin, one of the principal active ingredients in licorice root, is present in the root at concentrations ranging from 6 to 14 percent. Glycyrrhizin, along with other extractable matter, is obtained by comminuting licorice root, treating the root with hot water or steam, and recovering the water soluble extractives. These primary root extracts have pH values between about 5 and about 6, and glycyrrhizin generally constitutes about 10–35% of the extractive solids.

Glycyrrhizic acid, obtained by acidifying glycyrrhizin, can be ammoniated to provide ammoniated glycyrrhizin, by replacing one or more of the three acid hydrogen atoms with ammonium. Ammoniated glycyrrhizin therefore includes a mono-ammoniated product, a di-ammoniated product, and, at least theoretically, a tri-ammoniated product. Ammoninated glycyrrhizin is produced in a refinement process in which glycyrrhizic acid is recovered from the root extract. Ammoniated glycyrrhizin has a sweetness value of about 50 times as great as sucrose, as does glycyrrhizin itself. In addition to its intense sweetness, ammoniated glycyrrhizin does possess the characteristic licorice flavor albeit at reduced intensity. Ammoniated glycyrrhizin has been used to potentiate the sweetness of sucrose in sucrose-containing foods (U.S. Pat. No. 3,282,706), and to potentiate chocolate flavor (U.S. Pat. No. 3,356,505). According to each of these patents ammoninated glycyrrhizin is used as a potentiator at levels sufficiently low that the characteristic licorice flavor is not imparted to the final product. U.S. Pat. No. 3,851,073 describes a sweetening agent comprising ammoniated glycyrrhizin and a 5'-nucleotide in an amount sufficient to repress the licorice flavor of the ammoniated glycyrrhizin.

Heretofore, licorice root has been processed commercially almost exclusively for its water soluble extracts. As noted above, glycyrrhizin is contained in the aqueous extract derived from licorice root. Of course, substantial amounts of solid residue remain after removal of water-soluble material from the root. The solid residue, or spent licorice root, has posed a problem of disposal, and considerable thought has gone into finding acceptable uses for spent root. Spent root has been treated with alkali to produce an aqueous alkaline solution having a pH of at least 10 to obtain therefrom a complexing agent which has been combined with trace metals to form valuable micronutrients. This is described in U.S. Pat. No. 3,574,592. By and large, however, those in the art have considered extracts containing glycyrrhizin to be the extracts of value from licorice root, and once all appreciable levels of this material have been extracted from licorice root, the spent root is viewed as a by-product.

As environmental considerations heighten, and as the cost of unprocessed licorice root and extraction costs escalate, it has become increasingly imperative to reduce the amount of spent root ultimately discarded, and to isolate other materials of commercial value from spent root. To this end, it has been found that a new class of natural, glycyrrhizin-free fractions may be obtained from spent licorice root. These new glycyrrhizin-free fractions have surprisingly been found to possess the flavor potentiating property of glycyrrhizin without having its intense sweetness and characteristic licorice flavor. In addition, the glycyrrhizin-free fractions have been found to possess specific surface active and adsorptive properties rendering them useful as wetting, foaming, emulsifying, dispersing and settling agents, all of the foregoing properties testifying to the unique character of the new products.

DESCRIPTION OF THE PREFERRED EMBODIMENTS

This invention relates to a process for the production of selected glycyrrhizin-free (deglycyrrhizinated) fractions from spent licorice root, and more particularly to deglycyrrhizinated natural flavorants, flavor potentiators and adjuvants, and surface active agents, etc., essentially comprising deglycyrrhizinated fractions. As used in the specification and claims, the term "deglycyrrhizinated fraction" refers to and identifies compositions obtained from spent licorice root which are essentially free of glycyrrhizin and lack the flavor characteristic of licorice. It is most surprising, and contrary to all previous knowledge in the art, to find that deglycyrrhizinated fractions obtained from licorice root which lack the characteristic licorice flavor, have utility as flavorants and flavor potentiating adjuvants when all previous experience with licorice root extracts indicates that it is glycyrrhizin which provides sweetness, and flavor potentiation and elements of licorice flavor, on which use of conventional licorice root extracts is based. Further, it is surprising to find that the deglycyrrhizinated fractions exhibit other useful properties for which conventional licorice root extracts are not used.

One aspect of the present invention provides a process for recovery of deglycyrrhizinated fractions from water insoluble licorice root residue remaining after extraction of fresh licorice root to obtain primary root extracts having pH values between about 5 and about 6 which comprises:

(a) treating the water insoluble residue with an aqueous alkaline extractant producing an aqueous alkaline extract having a pH less than 10 and an insoluble residue;

(b) separating and isolating said aqueous alkaline extract and said insoluble residue;

(c) treating the aqueous alkaline extract with sufficient acid to acidify the extract to a pH of from about 2 to about 6, forming an acid soluble fraction and an acid insoluble residue;

(d) separating and isolating said acid soluble fraction and said acid insoluble residue;

(e) treating the acid insoluble residue with sufficient alkali to solubilize and alkalify the residue to a pH of from about 8 to less than 10 forming an alkali soluble fraction, and recovering said acid soluble fraction and said alkali-soluble fraction, said fractions being essentially glycyrrhizin-free, lacking the flavor characteristic of licorice.

As mentioned above, the solid residue remaining after water soluble extracts have been recovered from fresh licorice root is known in the art as "spent root". Actually, the term "spent root" is a misnomer, because, while the principal material of value, i.e. glycyrrhizin, is recovered from fresh root in primary extraction, and the root may be "spent", or nearly so, in terms of its glycyrrhizin content, it has been found that the residue remaining after primary extraction is not "spent" in terms of materials other than glycyrrhizin, and that valuable deglycyrrhizinated materials may be recovered from so-called spent root with carefully controlled and orchestrated extraction and fractionation.

Licorice root, a product of nature, is a complex material and many techniques have been used in an effort to obtain the maximum yield of glycyrrhizin from licorice root. Generally, hot water and/or steam is used in extraction of fresh root. However, throughout the years, a variety of agents have been used in an attempt to increase the yield of glycyrrhizin obtained from fresh root. Typical of such efforts are the procedures outlined in U.S. Pat. Nos. 1,389,663; 1,849,569; and 2,058,019 and British patent specification No. 988. For the most part, procedures such as those described in the enumerated references rely on addition of alkali, acid, or both and/or other chemical agents to hot water and/or steam to increase the yield of glycyrrhizin from a given quantity of fresh licorice root.

It is recognized in the art that licorice root possesses tremendous buffering capacity. That is, the pH of an extracting medium used to recover water soluble constituents from fresh root may vary substantially yet the primary extract recovered will have a pH in the range of about 5 to about 6. For example, unbuffered aqueous extractants having a pH of from about 3 to about 12 can be used in extraction of fresh root and, because of the buffering capacity of the root, the primary water soluble extracts recovered will have a pH between about 5 and about 6. As a corollary, spent root obtained after extraction of fresh root with an aqueous extractant having a pH in the range of 3 to 12 will not differ substantially regardless of the precise pH of the extractant. Certainly, such variance as may be found in the constituents in spent root from sample to sample can no more be attributed to differences in the pH of the extractant used in obtaining the primary extract than to differences inherent in various licorice root samples treated.

In view of the foregoing, it will be recognized that the most appropriate manner in which to define spent root which may properly be treated by the present invention is in terms of spent root as obtained from extraction of fresh licorice root in which the primary root extract obtained has a pH between about 5 and about 6. In other words, spent root obtained in any procedure for extraction of fresh licorice root in which the primary extraction of water soluble materials from the root is completed with an extractant having a pH ranging from about 3 to about 12 and in which the extract of water soluble material has a pH of about 5 to about 6, may be properly treated according to the present invention to obtain the deglycyrrhizinated products described in detail herein.

Considered in greater detail, the process of this invention comprises treating water insoluble residue (spent root) remaining after extraction of fresh licorice root with an alkaline extractant to produce an aqueous alkaline extract having a pH less than 10, preferably a pH of about 7 to 9. Any water soluble alkaline material may be used for extraction of spent root, so long as sufficient alkali is provided to alkalify the aqueous alkaline extract to a pH less than 10, and include sodium hydroxide, potassium hydroxide, ammonium hydroxide, trisodium phosphate and sodium silicate. Sodium hydroxide is particularly preferred.

No special conditions are required for initial alkaline extraction of spent root. Elevated temperatures and pressures above atmospheric may be used to facilitate the process. The alkaline extraction is most expeditiously carried out at temperatures of at least 220° F., preferably from about 275° F. to about 285° F. and under pressure of from about 40 to 45 psig. The extract recovered after alkaline extraction, as stated above, has a pH of less than 10, preferably from about 7 to 9, and is reserved for further treatment. The insoluble residue remaining after alkaline extraction may be disposed of in conventional manners.

The aqueous alkaline extractant is further treated with sufficient acid to acidify the extract to a pH of about 2 to 6, preferably below about 5, forming an acid soluble fraction and an acid insoluble residue. No special conditions are required for the acidification of the alkaline extract, although it is preferred that acidification be carried out at temperatures from about 100° F. to about 140° F. Acids useful in acidification of the alkaline extract include mineral acids such as sulfuric, hydrochloric and phosphoric acids, and a large number of organic acids which are sufficiently soluble and possess an ionization constant sufficiently high to provide the required hydrogen ion concentration. Organic acids, including but not limited to, acetic, butyric, citric, fumaric, glycolic, lactic, malic, oxalic, propionic, succinic, tartaric and vinylacetic acids may be used. It will be appreciated by those in the art, that the selection of acid and the amount of acid useful for acidification at this juncture in the process provide the possibility of considerable variance in characteristics and attributes of the resultant product. More will be said about this subject; suffice it to say that the combination of ionization constant and solubility of the acid selected for acidification must be sufficient to produce an acid soluble fraction having a pH from about 2 to 6, preferably below 5.

Considering acidification of the alkaline extract of spent root from another point of view, it will be appreciated that treatment of the aqueous alkaline extract to acidify the extract to a pH of about 2 to 6, has the effect of precipitating acid insoluble materials from the aqueous alkaline extract in addition to producing an acid soluble fraction. The composition of the components in the acid soluble fraction separated in this manner is now known with precision; infra-red analysis, however, indicates that the materials consist largely of various resinous compounds present in fresh or native root which are insoluble in water but which have been rendered soluble by the foregoing procedure.

The acid soluble fraction and the acid insoluble portion of the alkaline extract may be separated and isolated by conventional methods such as by filtration.

The acid insoluble residue of the alkaline extract is next treated with sufficient alkali to alkalify the residue to a pH of about 8 to less than 10, preferably about 8.5, forming an alkali soluble fraction. Again, no special conditions are required for the alkalification of the acid insoluble residue, although it is preferred that alkalification be carried out at temperatures of from about 90° F. to about 120° F. Alkalies useful in alkalification of the acid insoluble residue include ammonium hydroxide, potassium hydroxide and sodium hydroxide, and a large number or organic bases which are sufficiently soluble and possess an ionization constant sufficiently high to provide the required hydroxyl ion concentration. Organic bases include, but are not limited to, alanine, butylamine, diethylamine, ethanolamine, glycine, methylamine, piperidine, sarcosine and trimethylene diamine. The selection of alkali used for alkalification provides the possibility of considerable variance in characteristics and attributes of the resultant product, as will be discussed in greater detail hereafter. It is necessary, however, that the combination of ionization constant and solubility of the alkali selected for alkalification be sufficient to produce an alkali soluble extractant having a pH from about 8 to less than 10, preferably about 8.5. It is also necessary that the alkali selected for alkalification form a salt with the acid insoluble residue which is soluble in water or whatever other medium is chosen to make the solution.

The acid soluble fraction and the alkali soluble fraction are recovered in solution form and may be used in that form, or, if desired, may be concentrated or dried as by spray drying. As has been mentioned previously, the acid soluble fraction and the alkali soluble fraction are each essentially glycyrrhizin free. That is, the acid soluble fraction and the alkali soluble fraction lack the flavor characteristic of licorice and do not possess the intense sweetness usually associated with materials derived from licorice root.

The useful products recovered in the foregoing process may be defined as the deglycyrrhizinated acid soluble fraction and the deglycyrrhizinated alkali soluble fraction of the water insoluble licorice root residue remaining after extraction of fresh licorice root, said deglycyrrhizinated fractions lacking the intense sweetness of glycyrrhizin and being essentially free of flavor characteristic of licorice. More particularly, the product of the foregoing process may be defined as deglycyrrhizinated fractions from water insoluble licorice root residue remaining after extraction of fresh licorice root comprising:

(a) the essentially glycyrrhizin-free acid soluble fraction obtained on acidification to a pH of about 2 to 6, preferably below 5, of the aqueous alkaline extract having a pH less than 10 recovered on extraction of the water insoluble residue with an aqueous alkaline extractant, and (b) the essentially glycyrrhizin-free alkali soluble fraction obtained on alkalification to a pH of about 8 to less than 10, preferably about 8.5, of the acid insoluble residue formed on acidification to a pH of about 2 to 6 of the aqueous alkaline extract having a pH of less than 10 recovered on extraction of the water insoluble residue with an aqueous alkaline extractant;

said essentially glycyrrhizin-free fractions lacking the intense sweetness of glycyrrhizin and being essentially free of the flavor characteristic of licorice.

A most significant characteristic of the acid soluble fraction and the alkali soluble fraction is that they are each essentially glycyrrhizin free or deglycyrrhizinated fractions of licorice root. The most obvious manner in which to quantify this characteristic or property is by taste. Since glycyrrhizin provides the intense sweetness that is part of licorice flavor, absence of this highly characteristic flavor in fractions derived from licorice root is indicative of a glycyrrhizin-free product. There are more sophisticated means to determine the presence of glycyrrhizin such as the Houseman assay; however, this assay method must be modified when analyzing materials made by processes other than simple aqueous extraction of virgin licorice root, which it was particularly designed to analyze. Deglycyrrhizinated fractions of licorice root as discussed herein would analyze less than 5%, usually about 3%, glycyrrhizin by a modified Houseman assay, and would be free of the characteristic flavor of licorice by taste test. In contrast, primary licorice extracts typically assay 20–25% glycyrrhizin by Houseman assay.

Another surprising attribute of the acid soluble fraction and the alkali soluble fraction of this invention in addition to their lack of the licorice flavor, is that they individually retain a degree of sweetness, albeit the intense sweetness characteristic of glycyrrhizin and ammoniated glycyrrhizin is not present in the fractions. This is especially surprising in view of the discovery that if the acid soluble fraction and the alkali soluble fraction are combined, the resultant product has not enhanced sweetness and some characteristic licorice flavor, even though the glycyrrhizin content of the mixture remains very low.

The acid soluble and alkali soluble deglycyrrhizinated fractions of this invention have utility over an extremely broad spectrum. Licorice extract, glycyrrhiza and ammoniated glycyrrhiza have all been characterized as generally recognized as safe (GRAS) for many years. Since the deglycyrrhizinated fractions of this invention are derived from the same native root as the foregoing materials, they too should achieve GRAS status if obtained through techniques which employ materials which conform to standards of the *Food Chemical Codex* (FCC). Thus, one area of utility for the deglycyrrhizinated extracts lies in the field of natural flavorants, flavor potentiators, and adjuvants.

In the area of potential utility as natural flavorants, flavor potentiators and adjuvants, variation in the characteristics of the deglycyrrhizinated fractions may be achieved depending on the precise agents selected for acidification and alkalification in the process described above. That is, the particular acid or alkali or combination of acids or alkalis used in acidification and alkalification will have a bearing on flavor characteristics and properties of the resultant deglycyrrhizinated fractions. Of course, in order that the deglycyrrhizinated fractions of this invention may qualify for GRAS status, it is necessary that the particular acid and alkali used in producing the fractions as well as all other materials used in the overall process, comply with the FCC standards for all edible materials.

For example, an acid soluble deglycyrrhizinated fraction obtained with citric acid acidification of the aqueous alkaline extract recovered on extraction of the water insoluble residue remaining after initial extraction of fresh licorice root will have flavor characteristics different from a similar fraction obtained with mineral acid acidification. Likewise, an alkali soluble deglycyrrhizinated fraction obtained with sodium hydroxide alkalification of the acid insoluble residue formed on citric acid acidification of the aqueous alkaline extract recovered on extraction of the water insoluble residue remaining after initial extraction of fresh licorice root will have flavor characteristics different from a similar fraction obtained with an organic alkaline material. Therefore, the aspect of this invention which relates to food grade materials contemplates acid soluble and alkali soluble deglycyrrhizinated fractions prepared with any acid or alkali or combination of acids or alkalis which comply with FCC Food Chemical Codex standards for edible materials.

The complete scope of utility of the acid soluble and alkali soluble deglycyrrhizinated fractions as natural flavorants, flavor potentiators and adjuvants has not been determined; however, it is known that the deglycyrrhizinated acid soluble fraction formed on citric acid acidification has utility in the beverage industry, serving as a flavor enhancer for fermented beverages such as beer and wine; this fraction also has foaming properties and enhances flavors in soft drinks. The alkali soluble deglycyrrhizinated fraction formed with citric acid acidification and sodium hydroxide alkalification has flavor enhancing utility in coffee, puddings, pie fillings, syrups and tobacco products. The alkali soluble deglycyrrhizinated fraction formed with phosphoric acid acidification and sodium hydroxide alkalification has flavor enhancing utility in meats.

The acid soluble deglycyrrhizinated fraction and the alkali soluble deglycyrrhizinated fraction may be added to products as natural flavorants, flavor potentiators and adjuvants at levels sufficient to provide the desired effect. As will be appreciated, the amount of a particular deglycyrrhizinated fraction required in a given product will vary depending on a variety of factors including the presence of any undesirable flavor in the product to be masked, the intensity of flavor generally acceptable in the product, the nature of the flavor of the product and other factors. In general, an acceptable effect can be achieved with as little as 0.005% or as much as 5%, preferably about 0.02% to about 1%, by weight, based on the weight of the product, of the deglycyrrhizinated fractions. Concentrates containing up to about 60% of the deglycyrrhizinated fractions may be used in food products, a finished food product flavored with such concentrates typically containing about 0.02% to about 1%, by weight of the deglycyrrhizinated fractions. One aspect of the invention thus contemplates a method of flavoring and/or enhancing or potentiating the flavor of food products with acid soluble and alkali soluble deglycyrrhizinated fractions of spent licorice root.

The acid soluble and alkali soluble deglycyrrhizinated fractions have utility in fields other than as flavor enhancers, etc. In such cases, preparation of the fractions is as described above except that it is not necessary that the acid or alkali used in acidification and alkalification comply with FCC Food Chemical Codex standards, and any grade acid or alkali may be used. Deglycyrrhizinated fractions formed with such acids and alkalis have been found to have use as surface active agents including wetting, foaming, emulsifying, dispersing and settling agents; other uses undoubtedly exist but have not as yet been elucidated. In view of the broad range of surface active properties which the deglycyrrhizinated fractions have been found to possess, and the wide spectrum of materials with which the deglycyrrhizinated fractions may have utility, it is difficult to express precise usage levels for the deglycyrrhizinated fractions; however, in general, acceptable surface active effects can be achieved with from about 0.05% to about 5%, by weight, based on the solids content of the material treated, of the deglycyrrhizinated fractions.

The following examples illustrate preparation and utility of the deglycyrrhizinated fractions.

EXAMPLE 1

Water insoluble licorice root residue remaining after aqueous extraction of fresh licorice root at elevated temperatures and pressure in which the aqueous extractant had a pH of 6 and in which the primary extract of water soluble materials had a pH of 5.2, was extracted with a dilute aqueous solution of NaOH at a temperature of 285° F. and pressure of 45 psig. The weight ratio of water to spent root in the aqueous solution of NaOH is 5, and the amount of NaOH used is 2.7%, by weight, of the dry root solids. 15% of the spent root mass was solubilized, and a dilute (2.65%, by weight) solution of the solute was separated from the insoluble root by filtration. The aqueous alkaline solution recovered had a pH of 8.5, and had a sweet flavor with resinous character, and only a very mild hint of licorice flavor by taste test.

EXAMPLE 1A

Water insoluble licorice root residue remaining after aqueous alkaline extraction of fresh licorice root following the procedure of U.S. Pat. No. 2,058,019 in which the extractant had a pH of 11 and the primary extract obtained had a pH of 5.9, was extracted with a dilute aqueous solution of NaOH at a temperature equivalent to 285° F. and pressure of 45 psig. The weight ratio of water to spent root in the aqueous solution of NaOH is 15, and the amount of NaOH used is 2.25%, by weight, of the dry root solids. 13.7% of the spent root mass was solubilized, and a dilute (1.13%, by weight) solution of the solute was separated from the insoluble root by filtration. The aqueous alkaline solution recovered had a pH of 8.7, and had a sweet flavor with resinous character, and only a very mild hint of licorice flavor by taste test.

EXAMPLE 2

The aqueous alkaline solution of Example 1 was concentrated to 10% solids, by weight, and treated at a temperature of 120° F. with 27 pounds of $H_2SO_4$(93%) per 100 pounds of solids in the solution to reduce the pH from 8.4 to 2.9. After brief stirring to insure homogeneity, the resultant slurry was separated by filtration producing an acid soluble fraction and an acid insoluble residue. The acid soluble fraction was recovered, and the acid insoluble residue was mixed with an equal weight of water and NaOH was added at a temperature of 110° F. with stirring to form an alkali soluble fraction having a pH of 9.8.

EXAMPLE 2A

The aqueous alkaline solution of Example 1A was treated in the manner described in Example 2, and the acid soluble fraction and the alkali soluble fraction recovered were indistinguishable from those products obtained in Example 2.

EXAMPLE 3

The aqueous alkaline solution of Example 1 was concentrated to 10% solids, by weight, and treated at a temperature of 120° F. with 91 pounds of $H_3PO_4$(75%) per 100 pounds of solids in the solution to reduce the pH from 8.4 to 2.9. After brief stirring to insure homogeneity, the resultant slurry was separated by filtration producing an acid soluble fraction and an acid insoluble residue. The acid soluble fraction was recovered, and the acid insoluble residue was mixed with an equal weight of water and NaOH was added at a temperature of 110° F. with stirring to form an alkali soluble fraction having a pH of 9.

EXAMPLE 4

The aqueous alkaline solution of Example 1 was concentrated to 10% solids, by weight, and treated at a temperature of 120° F. with 92 pounds of food grade citric acid (100%) per 100 pounds of solids in the solution to reduce the pH from 8.4 to 3.2. After brief stirring to insure homogeneity, the resultant slurry was separated by filtration producing an acid soluble fraction and an acid insoluble residue. The acid soluble fraction was recovered, and the acid insoluble residue was mixed with an equal weight of water and food grade NaOH was added at a temperature of 110° F. with stirring to form an alkali soluble fraction having a pH of 8.5. The acid soluble fraction recovered had a pH of 3.2 and a slight sweet-sour taste, but no flavor characteristic of licorice was detected by taste test. The alkali soluble fraction recovered had a pH of 8.5, but no flavor characteristic of licorice was detected by taste test. Combinations of the acid soluble fraction and the alkali soluble fraction in various proportions produced mixtures having a spectrum of flavors including mixtures in which the distinct flavor characteristic of licorice was found by taste test.

EXAMPLE 5

An imitation vanilla was formed by mixing 1 part, by weight, ethyl vanillin, food grade; 2.5 parts, by weight, vanillin, food grade, 40 parts, by volume, propylene glycol U.S.P.; and 56 parts, by volume, of a 25%, by weight aqueous solution of the alkali soluble fraction of Example 4. The mixture was formed by heating the propylene glycol at 140° F., adding the vanillin and ethyl vanillin with stirring until completely dissolved and adding, with stirring, the solution of the alkali soluble fraction of Example 4. The resultant imitation vanilla was fivefold stronger in vanilla flavoring than household strength baking vanilla extract. For comparison, a vanillin composition was prepared without the alkali soluble fraction of Example 4. Each formulation was added to simple syrup at levels of 0.5 to 1%, by weight, and in side by side taste tests the formulation containing the alkali soluble fraction of Example 4 was found to possess improved flavor and aroma of vanilla.

EXAMPLE 6

The following formulations illustrate imitation flavorants prepared with the alkali soluble fraction of Example 4. Each of the flavorants find use at levels such that a manufactured food product containing the flavorant would contain about 0.002 to 0.05%, by weight, of the alkali soluble fraction.

| | | % |
|---|---|---|
| A. | Imitation Maple Flavor | |
| | Cyclotene | 0.4 |
| | Palatone | 0.4 |
| | Vanillin | 2 |
| | Coffee extract | 1 |
| | Oleoresin fenugreek | .15 |
| | Alkali soluble fraction | 10 |
| | Propylene glycol | 71.2 |
| B. | Imitation Low-Calorie Maple Flavored Syrup | % |
| | Imitation maple flavor of formulation A | 0.1 |
| | Propylene glycol alginate, | |
| | high viscosity | 0.8 |
| | Saccharin | 0.8 |
| | Alkali soluble fraction | 0.5 |
| | Salt | 0.1 |
| | Sodium benzoate | 0.1 |
| | Potassium sorbate | 0.1 |
| | Citric acid, hydrous | 0.025 |
| | Water | 98.195 |
| C. | Vegetable beef soup (instant powder) | % |
| | Beef fat | 0.5 |
| | Salt | 34 |
| | Imitation beef paste | 0.5 |
| | Autolyzed yeast extract | 0.5 |
| | Calcium silicate synthetic | 0.5 |
| | Alkali soluble fraction powder | 0.2 |
| | Dehydrated garlic powder | 0.5 |
| | Dehydrated onion powder | 9.0 |
| | Toasted onion powder | 4.0 |
| | Parsley flakes | 0.3 |
| | Celery seed ground | 0.5 |
| | Hydrolyzed vegetable protein | 7.0 |
| | Ribotide | 0.1 |
| | Monosodium glutamate | 10 |
| | Sugar | 32.4 |
| D. | Chocolate Syrup | % |
| | Sodium alginate | 0.2 |
| | Alkalized cocoa, 10-12% fat content | 10 |
| | Sodium benzoate | 0.1 |
| | Citric acid, to adjust pH to 4.5 | q.s. |
| | Vanillin | 0.1 |
| | Alkali soluble fraction | 1.0 |
| | Cane sugar | 54 |
| | Water | 34.6 |
| E. | Frankfurter Spice Flavor | % |
| | Oil coriander | 16 |
| | Oleoresin ginger | 35 |
| | Oleoresin mace | 40 |
| | Oil caraway | 5 |
| | Oil garlic | 0.5 |
| | Oil cinnamon bark | 3 |
| | Oil cloves | 0.5 |
| | Combine: | % |
| | above mixture | 8 |
| | Micro-Cel C | 2 |
| | Salt | 75 |
| | Hydrolyzed vegetable protein | 12 |
| | Alkali soluble fraction powder | 3 |

EXAMPLE 7

Two ml. of the acid soluble fraction of Example 4, containing 9% dissolved solids by weight, was placed in a glass, and a standard 12-ounce container of beer was poured into the glass; this corresponds to a treatment level of 0.05% of active material. Another 12-ounce container of the same brand of beer was poured into a like glass for comparison. Taste tests on the beer containing the acid soluble fraction of Example 4 showed marked enhancement of beer flavor over the untreated product. Foam height of beer containing the acid soluble fraction of Example 4 was initially higher than the untreated beer, and a foam cover of about ⅛ to ¼ inch thick persisted on the treated beer. The foam on untreated beer dissipated within a few minutes, while beer containing the acid soluble fraction of Example 4 was foam covered after 16 hours.

EXAMPLE 8

A dispersion of precipitated calcium carbonate (PURECAL O, USP) was prepared by stirring together equal weights of calcium and water. A stiff paste resulted. Varying amounts of the acid soluble fraction of Example 2 were added to samples of the CaCO3 paste with stirring and the nature of the resultant dispersion was analyzed to evaluate the surface active properties of the acid soluble fraction.

| Sample No. | Concentration (%) of Acid Soluble Fraction in CaCO3 Paste | Nature of Dispersion |
|---|---|---|
| 1 | 0 | Stiff paste |
| 2 | 1 | Stable flowable paste |
| 3 | 2 | Stable flowable paste |
| 4 | 3 | Stable flowable paste |
| 5 | 3.5 | Very flowable paste with solids separating from liquid. |
| 6 | 4 | Fluids, solids separate |

The range of effects observed was due to air displacement from the dispersion; air was observed bubbling out of the CaCO3 paste as the acid soluble fraction was incorporated. This procedure illustrates the marked surface active and wetting properties of the acid soluble fraction.

EXAMPLE 9

The acid soluble and alkali soluble fractions of Example 2 were blended in proportions to give pH values covering the range from 4 to 9.8, and these blends were made into aqueous solutions, each containing 4% total solids. An equal amount of sulfur was added to each sample, resulting in 50% dispersions of sulfur in the aqueous solutions of the acid soluble and alkali soluble fractions of Example 2 (4% by weight, based on sulfur).

| Sample No. | Blend of Acid Soluble and Alkali Soluble Fractions (pH) | Nature of Dispersion |
|---|---|---|
| 1 | 4 | Incomplete dispersion, lumps remaining |
| 2 | 5 | Incomplete dispersion, lumps remaining |
| 3 | 6 | Complete dispersion, soft and flowable |
| 4 | 7 | Complete dispersion, flowable, separates slowly |
| 5 | 8 | Complete dispersion, flowable, separates faster |
| 6 | 9 | Complete dispersion, flowable, separates quickly |
| 7 | 9.8 | Complete dispersion, flowable while agitated, settles to dense cake without agitation |

The nature of the dispersion formed in Samples 1–7 was analyzed to evaluate the surface active properties of the fractions produced in Example 2. The range of effects observed include both wetting properties and dispersing properties. It is seen that blends (Samples No. 2–6) of the two fractions of Example 2 exhibit properties that neither fraction alone (Samples No. 1 and 7) show in this system.

EXAMPLE 10

Blends of the acid soluble and alkali soluble fractions of Example 2 were prepared having a total solids concentration of 1% in water. These blends had a pH ranging from 3 to 9.8. Tall-form, four-ounce bottles were half filled with the respective blends, stoppered and shaken briefly. The following results were obtained at room temperature, illustrating a range of foaming properties at different pH levels:

| Sample No. | pH | Initial Foam Height (mm) | One-Hour Height (mm) | 24 Hours Height (mm) |
|---|---|---|---|---|
| 1 | 2.9 | 60 | 30 | 5 |
| 2 | 4 | 60 | 20 | 2 |
| 3 | 5 | 25 | 0 | 0 |
| 4 | 6 | 15 | 5 | 0 |
| 5 | 7 | 35 | 10 | 0 |
| 6 | 8 | 45 | 15 | 0 |
| 7 | 9 | 60 | 20 | 2 |
| 8 | 9.8 | 60 | 20 | 2 |

The high foam generation and stability with the acid-soluble fraction of Example 2 (sample no. 1 above) is similar to the result obtained in Example 7.

EXAMPLE 11

Equal volumes of water and low viscosity naphthenic mineral oil (100 SSU at 100° F.) were emulsified by stirring for 30 seconds at high speed in a blender, one sample containing the acid soluble fraction of Example 2, another the alkali soluble fraction of Example 2. A third sample contained no additives. The results are tabulated below.

| Sample No. | Additive | Appearance | | |
|---|---|---|---|---|
| | | Initial | One-Hr. | 24 Hrs. |
| 1 | None | Very grainy | Complete separation | Complete separation |
| 2 | 3%, by weight, based on wt. of oil, of acid soluble fractions. | oil-in-water emulsion with few oil globules | Emulsion remains with few oil globules | Distinct creaming with 5% of water at bottom and few oil globules |
| 3 | 3%, by weight, based on wt. of oil, of alkali soluble fraction | oil-in-water emulsion | oil-in-water emulsion | oil-in-water emulsion |

Oil-in-water emulsions formed initially in samples No. 2 and 3, the emulsion formed in sample No. 3 remained stable. Sample No. 2 appeared to convert to cream, indicative of potential application in water-in-oil systems such as cosmetic lotions, creams, etc.

Having thus described the invention, what is claimed is:

1. A process for recovery of deglycyrrhizinated fractions from water insoluble licorice root residue remaining after extraction of fresh licorice root with an unbuffered aqueous extractant having a ph of from about 3 to about 12 to obtain primary root extracts having pH values between about 5 and about 6 which comprises:
    (a) treating the water insoluble residue with an aqueous alkaline extractant producing an aqueous alkaline extract having a pH less than 10 and an insoluble residue;
    (b) separating and isolating said aqueous alkaline extract and said insoluble residue;
    (c) treating the aqueous alkaline extract with sufficient acid to acidify the extract to a pH of from about 2 to about 6, forming an acid soluble fraction and an acid insoluble residue;
    (d) separating and isolating said acid soluble fraction and said acid insoluble residue;
    (e) treating the acid insoluble residue with sufficient alkali to solubilize and alkalify the residue to a pH of from about 8 to less than 10 forming an alkali soluble fraction; and recovering said acid soluble fraction and said alkali soluble fraction, said fractions being essentially glycyrrhizin-free, lacking the flavor characteristic of licorice.

2. The process of claim 1 wherein the water insoluble residue is treated with an aqueous alkaline extractant to produce an aqueous alkaline extract having a pH of about 7 to 9.

3. The process of claim 1 wherein the water insoluble residue is treated with an aqueous alkaline extractant selected from the group consisting of sodium hydroxide, potassium hydroxide, ammonium hydroxide, trisodium phosphate and sodium silicate.

4. The process of claim 3 wherein the water insoluble residue is treated with an aqueous extractant of sodium hydroxide.

5. The process of claim 1 wherein the alkaline extraction is carried out at temperatures of at least 220° F. and under pressure up to about 40 to 45 psig.

6. The process of claim 1 wherein the aqueous alkaline extractant produced in (b) is treated with an acid selected from the group consisting of sulfuric, hydrochloric, phosphoric, acetic, butyric, citric, fumaric, glycolic, lactic, malic, oxalic, propionic, succinic, tartaric and vinylacetic acids.

7. The process of claim 6 wherein the aqueous alkaline extract is treated with sufficient acid to acidify the extract to a pH below about 5, and acidification is carried out at temperatures of from about 100° F. to about 140° F.

8. The process of claim 1 wherein the acid insoluble residue recovered in (d) is treated with an alkali selected from the group consisting of ammonium hydroxide, potassium hydroxide, sodium hydroxide, alanine, butylamine, diethylamine, ethanolamine, glycine, methylamine, piperidine, sarcosine and trimethylene diamine.

9. The process of claim 8 wherein the acid insoluble residue is treated with sufficient alkali to alkalify the residue to a pH of about 8.5, and alkalification is carried out at temperatures of from about 90° F. to about 120° F.

10. An essentially glycyrrhizin-free acid soluble fraction obtained by the process of claim 1.

11. A food product containing a flavoring or flavor potentiating amount of the deglycyrrhizinated fraction of claim 10.

12. An essentially glycyrrhizin-free alkali soluble fraction obtained by the process of claim 1.

13. A food product containing a flavoring or flavor potentiating amount of the deglycyrrhinated fraction of claim 12.

* * * * *

UNITED STATES PATENT AND TRADEMARK OFFICE
CERTIFICATE OF CORRECTION

PATENT NO. : 4,163,067
DATED : July 31, 1979
INVENTOR(S) : Harold A. Hartung

It is certified that error appears in the above-identified patent and that said Letters Patent are hereby corrected as shown below:

Line 3 of the Abstract, Page 1 "in" should read --is--.

Column 6, line 18 "not" should read -- both --.

Signed and Sealed this

Eleventh Day of December 1979

[SEAL]

Attest:

SIDNEY A. DIAMOND

Attesting Officer   Commissioner of Patents and Trademarks